(12) United States Patent
Veasey et al.

(10) Patent No.: US 10,576,214 B2
(45) Date of Patent: Mar. 3, 2020

(54) DISPLAY AND DRUG DELIVERY DEVICE

(71) Applicant: Sanofi, Paris (FR)

(72) Inventors: Robert Frederick Veasey, Warwickshire (GB); Paul Griffin, Worcestershire (GB); William Geoffrey Arthur Marsh, Buckinghamshire (GB); Matthew Meredith Jones, Warwick (GB); Richard James Vincent Avery, Mickelton (GB)

(73) Assignee: Sanofi, Paris (FR)

( * ) Notice: Subject to any disclaimer, the term of this patent is extended or adjusted under 35 U.S.C. 154(b) by 173 days.

(21) Appl. No.: 15/528,610

(22) PCT Filed: Nov. 24, 2015

(86) PCT No.: PCT/EP2015/077454
§ 371 (c)(1),
(2) Date: May 22, 2017

(87) PCT Pub. No.: WO2016/083347
PCT Pub. Date: Jun. 2, 2016

(65) Prior Publication Data
US 2017/0266384 A1    Sep. 21, 2017

(30) Foreign Application Priority Data
Nov. 24, 2014    (EP) ..................... 14306860

(51) Int. Cl.
*A61M 5/00*    (2006.01)
*A61M 5/315*    (2006.01)
(Continued)

(52) U.S. Cl.
CPC ............ *A61M 5/3157* (2013.01); *A61M 5/20* (2013.01); *A61M 5/31553* (2013.01);
(Continued)

(58) Field of Classification Search
CPC .... A61M 2005/3126; A61M 2205/581; A61M 2205/583; A61M 5/20; A61M 5/31548;
(Continued)

(56) References Cited

U.S. PATENT DOCUMENTS 5,503,628 A    4/1996    Fetters et al.
5,582,598 A *  12/1996    Chanoch .......... A61M 5/31551
                                                        222/309

(Continued)

FOREIGN PATENT DOCUMENTS

EP           0702970        3/1996
WO    WO 2006/114396     11/2006
(Continued)

OTHER PUBLICATIONS

International Preliminary Report on Patentability in International Application No. PCT/EP2015/077454, dated May 30, 2017, 9 pages.

(Continued)

*Primary Examiner* — Rebecca E Eisenberg
(74) *Attorney, Agent, or Firm* — Fish & Richardson P.C.

(57) ABSTRACT

The present disclosure is generally directed to a drug delivery device for selecting and dispensing a number of user variable doses of a medicament and to a non-numerical display for such a device. The display comprises a housing with at least one window, a dosing element movable relative to the housing during dose setting and/or dose dispensing, and a movable indicator element visible through the at least one window The indicator element is coupled to the dosing element and/or to the housing such that it moves not proportional to the dosing element.

12 Claims, 2 Drawing Sheets

(51) Int. Cl.
*A61M 5/20* (2006.01)
*A61M 5/31* (2006.01)

(52) U.S. Cl.
CPC ..... *A61M 5/31568* (2013.01); *A61M 5/31548* (2013.01); *A61M 5/31556* (2013.01); *A61M 5/31561* (2013.01); *A61M 5/31563* (2013.01); *A61M 5/31593* (2013.01); *A61M 2005/3126* (2013.01); *A61M 2205/581* (2013.01); *A61M 2205/583* (2013.01)

(58) Field of Classification Search
CPC .......... A61M 5/31553; A61M 5/31561; A61M 5/31563; A61M 5/31568; A61M 5/3157; A61M 5/31593

See application file for complete search history.

(56) References Cited

U.S. PATENT DOCUMENTS

2010/0168677 A1   7/2010  Gabriel et al.
2014/0046268 A1*  2/2014  Quinn ............... A61M 5/31541
                                                    604/209

FOREIGN PATENT DOCUMENTS

| WO | WO 2009/141004 | 11/2009 |
| WO | WO 2012/072535 | 6/2012 |
| WO | WO 2012/125876 | 9/2012 |

OTHER PUBLICATIONS

International Search Report and Written Opinion in International Application No. PCT/EP2015/077454, dated Jan. 25, 2016, 11 pages.

* cited by examiner

DISPLAY AND DRUG DELIVERY DEVICE

CROSS-REFERENCE TO RELATED APPLICATIONS

This application is a U.S. national stage application under 35 USC § 371 of International Application No. PCT/EP2015/077454, filed on Nov. 24, 2015, which claims priority to European Patent Application No. 14306860.9, filed on Nov. 24, 2014, the entire contents of which are incorporated herein by reference.

TECHNICAL FIELD

The present disclosure is generally directed to a non-numerical display for a drug delivery device and to a drug delivery device for selecting and dispensing a number of user variable doses of a medicament comprising such a housing.

BACKGROUND

Pen type drug delivery devices have application where regular injection by persons without formal medical training occurs. This may be increasingly common among patients having diabetes where self-treatment enables such patients to conduct effective management of their disease. In practice, such a drug delivery device allows a user to individually select and dispense a number of user variable doses of a medicament.

SUMMARY

The present disclosure is not directed to so called fixed dose devices which only allow dispensing of a predefined dose without the possibility to increase or decrease the set dose.

There are basically two types of drug delivery devices: resettable devices (i.e., reusable) and non-resettable (i.e., disposable). For example, disposable pen delivery devices are supplied as self-contained devices. Such self-contained devices do not have removable pre-filled cartridges. Rather, the pre-filled cartridges may not be removed and replaced from these devices without destroying the device itself. Consequently, such disposable devices need not have a resettable dose setting mechanism. The present disclosure is directed to reusable devices which allow resetting of the device and a replacement of a cartridge. Resetting of the device typically involves moving a piston rod or lead screw from an extended (distal) position, i.e. a position after dose dispensing, into a more retracted (proximal) position.

These types of pen delivery devices (so named because they often resemble an enlarged fountain pen) generally comprise three primary elements: a cartridge section that includes a cartridge often contained within a housing or holder; a needle assembly connected to one end of the cartridge section; and a dosing section connected to the other end of the cartridge section. A cartridge (often referred to as an ampoule) typically includes a reservoir that is filled with a medication (e.g., insulin), a movable rubber type bung or stopper located at one end of the cartridge reservoir, and a top having a pierceable rubber seal located at the other, often necked-down, end. A crimped annular metal band is typically used to hold the rubber seal in place. While the cartridge housing may be typically made of plastic, cartridge reservoirs have historically been made of glass.

The needle assembly is typically a replaceable double-ended needle assembly. Before an injection, a replaceable double-ended needle assembly is attached to one end of the cartridge assembly, a dose is set, and then the set dose is administered. Such removable needle assemblies may be threaded onto, or pushed (i.e., snapped) onto the pierceable seal end of the cartridge assembly.

The dosing section or dose setting mechanism is typically the portion of the pen device that is used to set (select) a dose. During an injection, a spindle or piston rod contained within the dose setting mechanism presses against the bung or stopper of the cartridge. This force causes the medication contained within the cartridge to be injected through an attached needle assembly. After an injection, as generally recommended by most drug delivery device and/or needle assembly manufacturers and suppliers, the needle assembly is removed and discarded.

A further differentiation of drug delivery device types refers to the drive mechanism: There are devices which are manually driven, e.g. by a user applying a force to an injection button, devices which are driven by a spring or the like and devices which combine these two concepts, i.e. spring assisted devices which still require a user to exert an injection force. The spring-type devices involve springs which are preloaded and springs which are loaded by the user during dose selecting. Some stored-energy devices use a combination of spring preload and additional energy provided by the user, for example during dose setting.

Unpublished patent application PCT/EP2014/056989 refers to a drug delivery device comprising a dose setting member which is axially constrained to a housing such that the dose setting member is rotatable with respect to the housing. A gauge element is interposed between the housing and the dose setting member. The gauge element is guided axially within the housing and is in threaded engagement with the dose setting member, such that the gauge element translates axially with respect to the housing and to the dose setting member upon a rotation of the dose setting member relative to the housing. The dose setting member further comprises a series of numbers visible through an aperture in the gauge element and a window in the housing. The numbers on the dose setting member constitute a numerical display and the movable gauge element may be seen as a non-numerical display indicated by its position relative to the housing the set dose.

In some cases, it may be desirable to indicate to a user that the device is in a certain state or phase of action, like reaching or being at the minimum dose position (e.g., a zero position) during dose dispensing. The present disclosure provides, in addition or as an alternative to a numerical display, a display capable of indicating a certain state or phase of action of a drug delivery device and a drug delivery device with such a display.

According to the disclosure, a non-numerical display for a drug delivery device comprises a housing with at least one window, a dosing element movable relative to the housing during dose setting and/or dose dispensing and a movable indicator element visible through the at least one window. The disclosure is based on the idea that a change in the movement, i.e. a non-steady motion, of the indicator element may be used to indicate a certain state or phase of action of a drug delivery device. Such a change in the movement of the indicator element is preferably effected by the indicator element being coupled to the dosing element and/or to the housing such that a movement of the dosing element relative to the housing is translated into a movement of the indicator element, which is not proportional to the movement of the dosing element. For example, the indicator element may change its speed and/or its direction of movement when reaching a certain state or phase of action, e.g. at the end of dose dispensing.

In a first embodiment the indicator element is coupled to the dosing element and/or to the housing such that a continuous movement of the dosing element relative to the housing is translated into a discontinuous movement of the indicator element. A discontinuous movement of the indicator element may comprise phases of differing speed of movement and/or phases of different direction of movement. The term 'continuous movement of the dosing element' is used herein as a reference to the different movement of the indicator element without limiting the disclosure to displays requiring that the dosing element permanently performs a continuous movement in use. Rather, the movement of the dosing element depends on the movement executed by a user in manually driven drug delivery devices and may vary in spring driven devices, too, for example due to non-uniform spring behavior or frictional effects.

According to a more specific embodiment, a continuous movement of the dosing element relative to the housing is translated into an intermittent movement of the indicator element. An example for an intermittent movement may include a movement in a first direction followed by a movement in a different direction. This includes cases where the different direction is a combination of the first direction with a further direction. As an alternative, a Geneva drive may translate a continuous movement of the dosing element relative to the housing into a discontinuous movement of the indicator element.

According to a further embodiment of the disclosure, the indicator element may be coupled to the housing such that, at least during one state or phase of movement, the indicator element is allowed to move axially with respect to the housing and is rotationally constrained to the housing. For example, the indicator element may be splined to the housing. In another state or phase of movement, relative rotation of the indicator element with respect to the housing may be allowed. Preferably, a continuous movement of the dosing element relative to the housing is translated into a pure axial movement during a first phase of the movement of the indicator element and into a combined axial and rotational movement during a second phase of the movement of the indicator element. For example, the indicator element may be guided within the housing in a track having a first, axially extending portion and a second, helical portion. In other words, the indicator element may start to rotate at a certain point during use of the drug delivery device, for example during dose dispensing when the set dose is completely or nearly completely dispensed from the device.

If the transition between the first, axially extending portion of the track and the second, helical portion of the track is stepped, i.e. a steep transition, relative movement of the dosing element and the indicator element may generate an audible and/or tactile signal, like a clicking sound. In a further embodiment of the disclosure, the indicator element may be guided within the housing in a track having at least two portions which are offset in a rotational direction (e.g. around the longitudinal axis of the device) by at least 5°, preferably by at least 25°, e.g. by at least 45°. A transition portion, e.g. a helical path, may be provided between the two portions to allow transition of the indicator element from the first portion of the track into the second portion of the track and vice versa.

For example, during dispense, the frictional contact with the dosing element, e.g. a number sleeve, applies torque to the indicator element, which is resisted by its spline connection with the housing. If the pitch of the e.g. helical section of the splines is very shallow, so that the indicator element tends to fall off the end of the spline at the end of dispense, it accelerates into the stepped spline and creates an audible click. This could be used with or without the visual feedback features described above.

In addition or as an alternative to the first embodiment an, e.g. continuous, movement of the dosing element relative to the housing may be translated into a movement with a first speed ratio during a first phase of the movement of the indicator element and into a movement with a second, different speed ratio during a second phase of the movement of the indicator element. In this embodiment, the indicator element may move on a linear path, but the axial distance by which it moves for each unit increases or decreases e.g. towards the end of dispensing. This may be achieved by varying the pitch on the dosing element if the dosing element is threaded to the indicator element. Preferably, the dosing element performs a rotational movement relative to the housing during dose setting and/or dose dispensing with the indicator element being in threaded engagement with the dosing element. The pitches chosen and the length over which they exist could easily be varied to suit the specification of the device. According to an embodiment of the disclosure, the pitch of the thread between the dosing element and the indicator element is larger towards the end of dose dispensing, i.e. with a small dose set, compared with the beginning of dose dispensing, i.e. with a larger dose set. For example, for users that require low doses, the increased indicator element travel at these dose values will make it easier for them to distinguish, and therefore use, the indicator element motion.

The display may further comprise a surface provided with a marking, which surface is located radially inwards of the indicator element, such that the indicator element shields the surface depending on the position of the indicator element relative to the housing. In other words, the indicator element either masks or reveals the marked surface depending on the position of the indicator element relative to the marked surface. The marked surface may have symbols, a color code or the like.

Further, the indicator element may comprise at least one region provided with a marking located adjacent to a region of the indicator element without this marking or with a different marking. An additional window provided in the housing is preferably arranged such that the region provided with the marking is visible through the additional window depending on the position of the indicator element relative to the housing. For example, the indicator element may begin to rotate as it nears the end of the dose dispensing, revealing a colored region that becomes visible through a window in the housing. This indicates to the user that the end of dose dispensing is about to be reached.

A drug delivery device for selecting and dispensing a number of user variable doses of a medicament comprises a non-numerical display as mentioned above and a cartridge containing a medicament.

In addition to the non-numerical display, the device may further comprise a numerical display for indicating a dose set by the dosing element. For example, the numerical display comprises a series of numbers provided on an outer surface of the dosing element and an aperture or window provided in the indicator element, such that the series of numbers is visible through the aperture or window of the indicator element and a window of the housing. If the dosing element and the indicator element are in threaded engagement, the pitch of the printed numbers must be adjusted to maintain alignment with the window of the indicator element.

Preferably, the dosing element is rotatable relative to the housing between a minimum dose position, e.g. a zero unit stop, and a maximum dose position. The minimum dose position may be defined by engagement of a rotational stop on the indicator element with a counter-stop on the dosing element and the maximum dose position may be defined by engagement of a rotational stop on the indicator element with a counter-stop on the dosing element. Thus, the indicator element and the dosing element have multiple functions.

In a preferred embodiment the drug delivery device has at least one numerical display and at least two non-numerical displays, preferably three non-numerical displays. For example, one of the non-numerical displays is coupled to the numerical display, such that they move with a constant speed ration and/or direction, whereas a further non-numerical display moves in a non-steady way relative to the numerical display. This allows giving different information to a user.

The term "medicament", as used herein, means a pharmaceutical formulation containing at least one pharmaceutically active compound, wherein in one embodiment the pharmaceutically active compound has a molecular weight up to 1500 Da and/or is a peptide, a protein, a polysaccharide, a vaccine, a DNA, a RNA, an enzyme, an antibody or a fragment thereof, a hormone or an oligonucleotide, or a mixture of the above-mentioned pharmaceutically active compound,
wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis,
wherein in a further embodiment the pharmaceutically active compound comprises at least one peptide for the treatment and/or prophylaxis of diabetes mellitus or complications associated with diabetes mellitus such as diabetic retinopathy,
wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivatives are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-($\omega$-carboxyheptadecanoyl)-des(B30) human insulin and B29-N-($\omega$-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:
H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group -Lys6-NH2 may be bound to the C-terminus of the Exendin-4 derivative;
or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2, des Pro36, Pro37, Pro38 [Met(O)14, Asp28] Exendin-4(1-39)-(Lys)6-NH2, H-(Lys)6-des Pro36, Pro37, Pro38 [Met(O)14, Asp28] Exendin-4(1-39)-(Lys)6-NH2, H-Asn-(Glu)5 des Pro36, Pro37, Pro38 [Met(O)14, Asp28] Exendin-4(1-39)-(Lys)6-NH2, H-Lys6-des Pro36 [Met(O)14, Trp(O2)25, Asp28] Exendin-4(1-39)-Lys6-NH2, H-des Asp28 Pro36, Pro37, Pro38 [Met(O)14, Trp(O2)25] Exendin-4(1-39)-NH2, H-(Lys)6-des Pro36, Pro37, Pro38 [Met(O)14, Asp28] Exendin-4(1-39)-NH2, H-Asn-(Glu)5-des Pro36, Pro37, Pro38 [Met(O)14, Trp(O2)25, Asp28] Exendin-4(1-39)-NH2, des Pro36, Pro37, Pro38 [Met(O)14, Trp(O2)25, Asp28] Exendin-4(1-39)-(Lys)6-NH2, H-(Lys)6-des Pro36, Pro37, Pro38 [Met(O)14, Trp(O2)25, Asp28] Exendin-4(S1-39)-(Lys)6-NH2, H-Asn-(Glu)5-des Pro36, Pro37, Pro38 [Met(O)14, Trp(O2)25, Asp28] Exendin-4(1-39)-(Lys)6-NH2;

or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region (CH) and the variable region (VH). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

BRIEF DESCRIPTION OF THE FIGURES

Non-limiting, exemplary embodiments of the disclosure will now be described with reference to the accompanying drawings, in which.

DETAILED DESCRIPTION

The display of the present disclosure may be used in various drug delivery devices, irrespective of whether the device is a disposable or reusable device or whether the device is manually driven or spring driven. In the following, the display is described with reference to an exemplary embodiment of a disposable spring driven drug delivery device. However, the display is not limited to use in such a drug delivery device.

Figure 1:
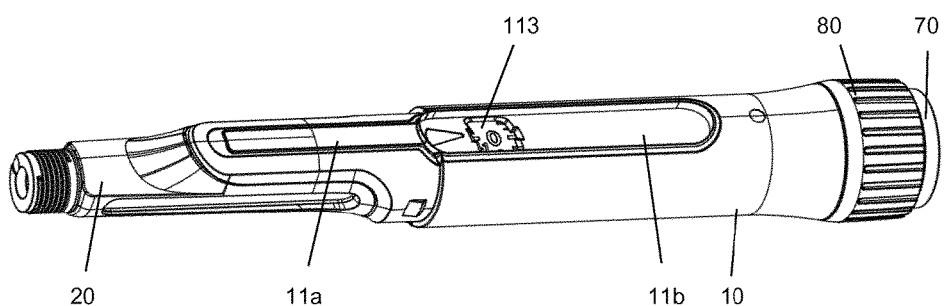
FIG. 1 shows a top view of a drug delivery device.
Figure 2:
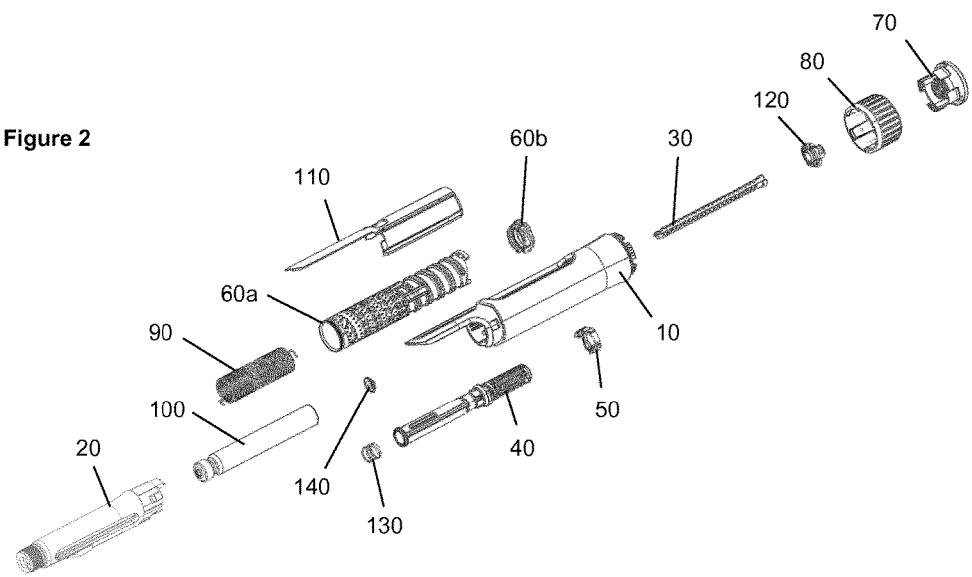
FIG. 2 shows an exploded view of the components of the device of FIG. 1.
Figure 3:
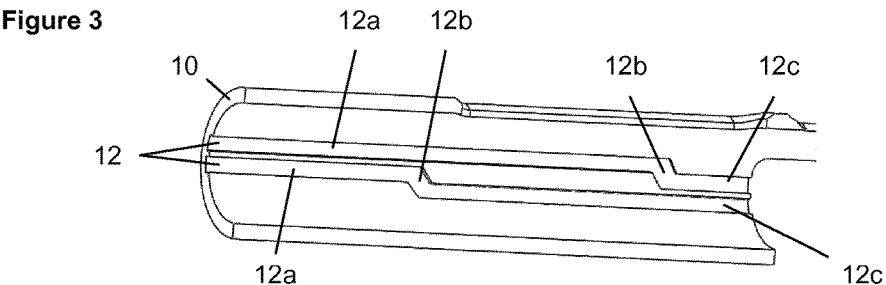
FIG. 3 shows a sectional view of the housing according to a first embodiment of the present disclosure.

FIG. 1 shows a drug delivery device in the form of an injection pen. The device has a distal end (left end in FIG. 1) and a proximal end (right end in FIG. 1). The component parts of the drug delivery device are shown in FIG. 2. The drug delivery device comprises a body or housing 10, a cartridge holder 20, a lead screw (piston rod) 30, a drive sleeve 40, a nut 50, a dose indicator (number sleeve) 60, a button 70, a dial grip or dose selector 80, a torsion spring 90, a cartridge 100, a gauge element 110, a clutch plate 120, a clutch spring 130 and a bearing 140. A needle arrangement (not shown) with a needle hub and a needle cover may be provided as additional components, which can be exchanged as explained above. All components are located concentrically about a common principal axis of the mechanism.

The housing 10 or body is a generally tubular element having a proximal end with an enlarged diameter. The housing 10 provides location for the liquid medication cartridge 100 and cartridge holder 20, windows 11a, 11b for viewing the dose number on the number sleeve 60 and the gauge element 110, and a feature on its external surface, e.g. a circumferential groove, to axially retain the dose selector 80. An insert comprises an inner thread engaging the piston rod 30. The housing 10 further has at least one internal, axially orientated slot or the like for axially guiding the gauge element 110. In the embodiment shown in the Figures, the distal end is provided with an axially extending strip partly overlapping cartridge holder 20. The Figures depict the housing 10 as a single housing component. However, the housing 10 could comprise two or more housing components which may be permanently attached to each other during assembly of the device.

Figure 5:
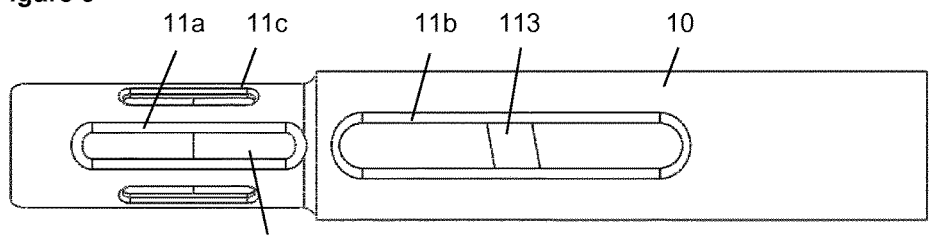
FIG. 5 shows a top view of a drug delivery device according to the first embodiment of the present disclosure in a first state.
Figure 6:
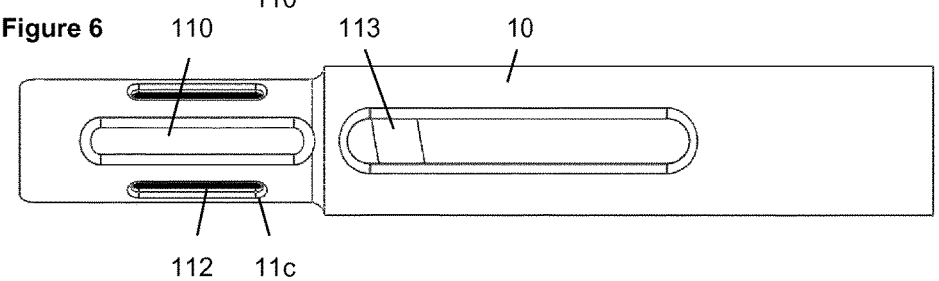
FIG. 6 shows a top view of the drug delivery device of FIG. 5 in a second state.

FIGS. 5 and 6 depict a housing 10 which is amended compared with the housing of FIGS. 1 and 2 in that additional windows 11c are provided extending in the axial direction parallel to window 11a. As the windows 11a, 11b, the additional windows 11c may be made as a translucent or transparent part of the housing 10 and may be designed as a lens. A portion of the gauge element 110 is visible through windows 11c as the gauge element 110 travels in the distal direction during dose dispensing as will be explained in more detail below. Vice versa, the gauge element 110 is moved out of the window 11c during dose setting. In FIG. 5 a non-marked portion of gauge element 110 is visible through each window 11c, whereas in FIG. 6 a marked portion, e.g. a colored portion 112, of gauge element 110 is visible through each window 11c. FIG. 6 represents the device in a minimum dose position (e.g., a_zero unit position) which is indicated by the marked portions 112 being visible through windows 11c.

The cartridge holder 20 is located at the distal side of housing 10 and permanently attached thereto. The cartridge holder may be a transparent or translucent component which is tubular to receive cartridge 100. The distal end of cartridge holder 20 may be provided with means for attaching a needle arrangement. A removable cap (not shown) may be provided to fit over the cartridge holder 20 and may be retained via clip features on the housing 10.

The piston rod 30 is rotationally constrained to the drive sleeve 40 via a splined interface. When rotated, the piston rod 30 is forced to move axially relative to the drive sleeve 40, through its threaded interface with the insert of housing 10. The lead screw 30 is an elongate member with an outer thread engaging the corresponding thread of the insert of housing 10. The interface comprises at least one longitudinal groove or track and a corresponding protrusion or spline of the driver 40. At its distal end, the lead screw 30 is provided with an interface for clip attachment of the bearing 140.

The drive sleeve 40 is a hollow member surrounding the lead screw 30 and arranged within number sleeve 60. It extends from an interface with the clutch plate 120 to the contact with the clutch spring 130. The drive sleeve 40 is axially movable relative to the housing 10, the piston rod 30 and the number sleeve 60 in the distal direction against the bias of clutch spring 130 and in the opposite proximal direction under the bias of clutch spring 130.

A splined tooth interface with the housing 10 prevents rotation of the drive sleeve 40 during dose setting. This interface comprises a ring of radially extending outer teeth at the distal end of drive sleeve 40 and corresponding radially extending inner teeth of the housing component 10. When the button 70 is pressed, these drive sleeve 40 to housing 10 spline teeth are disengaged allowing the drive sleeve 40 to rotate relative to housing 10. A further splined tooth interface with the number sleeve 60 is not engaged during dialing, but engages when the button 70 is pressed, preventing relative rotation between the drive sleeve 40 and number sleeve 60 during dispense. In a preferred embodiment this interface comprises inwardly directed splines on a flange on the inner surface of the number sleeve 60 and a ring of radially extending outer splines of drive sleeve 40. These corresponding splines are located on the number sleeve 60 and the drive sleeve 40, respectively, such that axial movement of the drive sleeve 40 relative to the (axially fixed) number sleeve 60 engages or disengages the splines to rotationally couple or decouple the drive sleeve 40 and the number sleeve 60.

A further interface of the drive sleeve 40 comprises a ring of ratchet teeth located at the proximal end face of drive sleeve 40 and a ring of corresponding ratchet teeth on the clutch plate 120.

The driver 40 has a threaded section providing a helical track for the nut 50. In addition, a last dose abutment or stop is provided which may be the end of the thread track or preferably a rotational hard stop for interaction with a corresponding last dose stop of nut 50, thus limiting movement of the nut 50 on the driver thread. At least one longitudinal spline of the driver 40 engages a corresponding track of the lead screw 30.

The last dose nut 50 is located between the number sleeve 60 and the drive sleeve 40. It is rotationally constrained to the number sleeve 60, via a splined interface. It moves along a helical path relative to the drive sleeve 40, via a threaded interface, when relative rotation occurs between the number sleeve 60 and drive sleeve 40 which is during dialing only. As an alternative, the nut 50 may be splined to the driver 40 and threaded to the number sleeve 60. A last dose stop is provided on nut 50 engaging a stop of drive sleeve 40 when a dose is set corresponding to the remaining dispensable amount of medicament in the cartridge 100.

The dose indicator or number sleeve 60 is a tubular element. The number sleeve 60 is rotated during dose setting (via dose selector 80) and dose correction and during dose dispensing by torsion spring 90. Together with gauge element 110 the number sleeve 60 defines a zero position ('at rest') and a maximum dose position. Thus, the number sleeve 60 may be seen as a dose setting member.

For manufacturing reasons, the number sleeve 60 of the embodiment shown in the Figures comprises a number sleeve lower 60*a* which is rigidly fixed to a number sleeve upper 60*b* during assembly to form the number sleeve 60. Number sleeve lower 60*a* and number sleeve upper 60*b* are separate components only to simplify number sleeve 60 mold tooling and assembly. As an alternative, the number sleeve 60 may be a unitary component. The number sleeve lower 60*a* is marked with a sequence of numbers, which are visible through the gauge element 110 and the openings 11*a*, 11*b* in the housing 10, to denote the dialed dose of medicament.

The number sleeve 60 in combination with gauge element 110 and window 11*b* of the housing 10 forms a numerical display which may be used in addition to the non-numerical display of the present disclosure.

Further, the number sleeve lower 60*a* has a portion with an outer thread engaging the gauge element 110. End stops are provided at the opposite ends of thread to limit relative movement with respect to the gauge element 110.

Clutch features which have the form of a ring of splines are provided inwardly directed on number sleeve upper 60*b* for engagement with splines of the button 70 during dose setting and dose correction. A clicker arm is provided on the outer surface of number sleeve 60 which interacts with the drive sleeve 40 and the gauge member 110 for generating a feedback signal. In addition, the number sleeve lower 60*a* is rotationally constrained to the nut 50 and to the clutch plate 120 via a splined interface comprising at least one longitudinal spline. Further, number sleeve lower 60*a* comprises an interface for attachment of the torsion spring 90.

The button 70 which forms the proximal end of the device is permanently splined to the dose selector 80. A central stem extends distally from the proximal actuation face of the button 70. The stem is provided with a flange carrying the splines for engagement with splines of the number sleeve upper 60*b*. Thus, it is also splined via splines to the number sleeve upper 60*b* when the button 70 is not pressed, but this spline interface is disconnected when the button 70 is pressed. The button 70 has a discontinuous annular skirt with splines. When the button 70 is pressed, splines on the button 70 engage with splines on the housing 10, preventing rotation of the button 70 (and hence the dose selector 80) during dispense. These splines disengage when the button 70 is released, allowing a dose to be dialed. Further, a ring of ratchet teeth is provided on the inner side of button flange for interaction with clutch plate 120.

The dose selector 80 is axially constrained to the housing 10. It is rotationally constrained, via the splined interface, to the button 70. This splined interface which includes grooves interacting with spline features formed by the annular skirt of button 70 remains engaged irrespective of the dose button 70 axial positions. The dose selector 80 or dose dial grip is a sleeve-like component with a serrated outer skirt.

The torsion spring 90 is attached at its distal end to the housing 10 and at the other end to the number sleeve 60. The torsion spring 90 is located inside the number sleeve 60 and surrounds a distal portion of the drive sleeve 40. The torsion spring 90 is pre-wound upon assembly, such that it applies a torque to the number sleeve 60 when the mechanism is at zero units dialed.

The action of rotating the dose selector 80, to set a dose, rotates the number sleeve 60 relative to the housing 10, and charges the torsion spring 90 further.

The cartridge 100 is received in cartridge holder 20. The cartridge 100 may be a glass ampoule having a moveable rubber bung at its proximal end. The distal end of cartridge 100 is provided with a pierceable rubber seal which is held in place by a crimped annular metal band. In the embodiment depicted in the Figures, the cartridge 100 is a standard 1.5 ml cartridge. The device is designed to be disposable in that the cartridge 100 cannot be replaced by the user or health care professional. However, a reusable variant of the device could be provided by making the cartridge holder 20 removable and allowing backwinding of the lead screw 30 and the resetting of nut 50.

The gauge element 110 of FIGS. 1 and 2 is constrained to prevent rotation but allow translation relative to the housing 10 via a splined interface. The gauge element 110 has a helical feature on its inner surface which engages with the helical thread cut in the number sleeve 60 such that rotation of the number sleeve 60 causes axial translation of the gauge element 110. This helical feature on the gauge element 110 also creates stop abutments against the end of the helical cut in the number sleeve 60 to limit the minimum and maximum dose that can be set.

The gauge element 110 has a generally plate or band like component having a central aperture 113 or window and two flanges extending on either side of the aperture. The flanges are preferably not transparent and thus shield or cover the number sleeve 60, whereas the aperture or window allows viewing a portion of the number sleeve lower 60*a*. Further, gauge element 110 has a cam and a recess interacting with the clicker arm of the number sleeve 60 at the end of dose dispensing.

Figure 4:
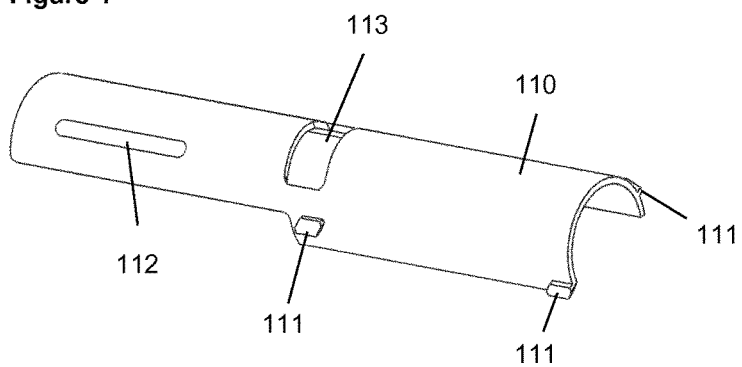
FIG. 4 shows a top view of a gauge element according to the first embodiment of the present disclosure.

FIGS. 3 to 6 show a first embodiment of the disclosure which involves the use of features which cause the gauge element 110 to deviate from a purely linear path at, or near to, the end of dose dispensing, i.e. the minimum dose position. This can be used to provide a visual or audible indication that the end of dose has been reached and/or increase the feedback provided by the gauge element 110 for small dose sizes. In this embodiment, the deviation from a linear path consists of a rotation about the main axis of the drug delivery device. The housing comprises two tracks 12 (splines) guiding the gauge element 110 which comprises four bosses 111 as shown in FIG. 4. In FIG. 4, the bosses 111 have two chamfered corners. Each track 12 comprises a first section 12*a* extending parallel to the main (longitudinal) axis of the drug delivery device and a second section 12*b* which is helical and a third portion 12c extending parallel to the main (longitudinal) axis of the drug delivery device, which is offset to the first portion 12a by about 15°. The different tracks 12a, 12b, 12c in which the bosses 111 are guided have the effect that the movement of the gauge element 110 is not proportional to the movement of the (rotating) number sleeve 60 due to the change from an axial movement relative to the housing into a helical movement and vice versa. Rather, a continuous rotational movement of the dosing element 60 relative to the housing 10 is translated into a discontinuous movement of the indicator element 110. As shown in FIGS. 4 and 6, the gauge element 110 has two regions 112 printed with a different color. Further, housing 10 has two additional windows 11c extending parallel to window 11a in the exemplary embodiment of FIGS. 5 and 6.

Due to this arrangement, the gauge element 110 begins to rotate as it nears the end of the dose, revealing colored regions 12 that become visible through two windows 11c in the housing 10. This indicates to the user that the end of dose is about to be reached. The splines 12 in the housing 10 that the gauge element 110 interacts with have a helical section which causes the rotation of gauge element 110. The helical motion of the gauge element 110 requires adjustment of the position of the printed numbers on the number sleeve lower 60a that become visible whilst the gauge element 110 is moving in the helical direction. In this embodiment, the pitch of the helix upon which the numbers lie would be slightly increased for units 0 to 9. During dispense, the frictional contact with the number sleeve lower 60a will tend to apply torque to the gauge element 110, which is resisted by its spline connection 12, 111 with the housing 10.

In a variation of this embodiment, the pitch of the helical section 12b of the splines can be made very shallow, so that the gauge element 110 tends to fall off the end of the spline 12 at the end of dispense. In this case, it would accelerate into the stepped spline and create an audible click. This could be used with or without the visual feedback features described above.

In addition to the non-numerical display provided by marked regions 112 of the gauge element 110 and the additional windows 11c, the drug delivery device comprises further non-numerical displays, namely the distal end of gauge element 110 being visible through window 11a depending on the axial position of the gauge element 110 relative to the housing 10 and the position of an aperture 113 in the gauge element 110 through which the numbers on number sleeve 60 are visible. As can be seen comparing FIGS. 5 and 6, the aperture 113 moves axially within the area defined by window 11b, such that the position of aperture 113 may be used to roughly indicate the actually set dose.

The clutch plate 120 is a ring-like component. The clutch plate 120 is splined to the number sleeve 60 via splines. It is also coupled to the drive sleeve 40 via a ratchet interface. The ratchet provides a detented position between the number sleeve 60 and drive sleeve 40 corresponding to each dose unit, and engages different ramped tooth angles during clockwise and anti-clockwise relative rotation. A clicker arm is provided on the clutch plate 120 for interaction with ratchet features of the button 70.

The clutch spring 130 is a compression spring. The axial position of the drive sleeve 40, clutch plate 120 and button 70 is defined by the action of the clutch spring 130, which applies a force on the drive sleeve 40 in the proximal direction. This spring force is reacted via the drive sleeve 40, clutch plate 120, and button 70, and when 'at rest' it is further reacted through the dose selector 80 to the housing 10. The spring force ensures that the ratchet interface between drive sleeve 40 and clutch plate 120 is always engaged. In the 'at rest' position, it also ensures that the button splines are engaged with the number sleeve splines, and the drive sleeve teeth are engaged with teeth of the housing 10.

The bearing 140 is axially constrained to the piston rod 30 and acts on the bung within the liquid medicament cartridge. It is axially clipped to the lead screw 30, but free to rotate.

With the device in the 'at rest' condition as shown in FIG. 1, the number sleeve 60 is positioned against its zero dose abutment with the gauge element 110 and the button 70 is not depressed. Dose marking '0 ' on the number sleeve 60 is visible through the window 11b of the housing 10 and gauge element 110, respectively.

The torsion spring 90, which has a number of pre-wound turns applied to it during assembly of the device, applies a torque to the number sleeve 60 and is prevented from rotating by the zero dose abutment.

The user selects a variable dose of liquid medicament by rotating the dose selector 80 clockwise, which generates an identical rotation in the number sleeve 60. Rotation of the number sleeve 60 causes charging of the torsion spring 90, increasing the energy stored within it. As the number sleeve 60 rotates, the gauge element 110 translates axially due to its threaded engagement thereby showing the value of the dialed dose. The gauge element 110 has flanges either side of the window area which cover the numbers printed on the number sleeve 60 adjacent to the dialed dose to ensure only the set dose number is made visible to the user.

A specific feature of this disclosure is the inclusion of a visual feedback feature in addition to the discrete dose number display typical on devices of this type. The distal end of the gauge element 110 creates a sliding scale through the small window 11a in the housing 10. As an alternative, the sliding scale could be formed using a separate component engaged with the number sleeve 60 on a different helical track.

As a dose is set by the user, the gauge element 110 translates axially, the distance moved proportional to the magnitude of the dose set. This feature gives clear feedback to the user regarding the approximate size of the dose set. The dispense speed of an auto-injector mechanism may be higher than for a manual injector device, so it may not be possible to read the numerical dose display during dispense. The gauge feature provides feedback to the user during dispense regarding dispense progress without the need to read the dose number itself. For example, the gauge display may be formed by an opaque element on the gauge element 110 revealing a contrasting colored component underneath. Alternatively, the revealable element may be printed with coarse dose numbers or other indices to provide more precise resolution. In addition, the gauge display simulates a syringe action during dose set and dispense.

The drive sleeve 40 is prevented from rotating as the dose is set and the number sleeve 60 rotated, due to the engagement of its splined teeth with teeth of the housing 10. Relative rotation must therefore occur between the clutch plate 120 and drive sleeve 40 via the ratchet interface.

The user torque required to rotate the dose selector 80 is a sum of the torque required to wind up the torsion spring 90, and the torque required to overhaul the ratchet interface. The clutch spring 130 is designed to provide an axial force to the ratchet interface and to bias the clutch plate 120 onto the drive sleeve 40. This axial load acts to maintain the ratchet teeth engagement of the clutch plate 120 and drive sleeve 40.

The torque required to overhaul the ratchet in the dose set direction is a function of the axial load applied by the clutch spring 130, the clockwise ramp angle of the ratchet teeth, the friction coefficient between the mating surfaces and the mean radius of the ratchet interface.

As the user rotates the dose selector 80 sufficiently to increment the mechanism by one increment, the number sleeve 60 rotates relative to the drive sleeve 40 by one ratchet tooth. At this point the ratchet teeth re-engage into the next detented position. An audible click is generated by the ratchet re-engagement, and tactile feedback is given by the change in torque input required.

Relative rotation of the number sleeve 60 and the drive sleeve 40 is allowed. This relative rotation also causes the last dose nut 50 to travel along its threaded path, towards its last dose abutment on the drive sleeve 40.

With no user torque applied to the dose selector 80, the number sleeve 60 is now prevented from rotating back under the torque applied by the torsion spring 90, solely by the ratchet interface between the clutch plate 120 and the drive sleeve 40. The torque necessary to overhaul the ratchet in the anti-clockwise direction is a function of the axial load applied by the clutch spring 130, the anti-clockwise ramp angle of the ratchet, the friction coefficient between the mating surfaces and the mean radius of the ratchet features. The torque necessary to overhaul the ratchet must be greater than the torque applied to the number sleeve 60 (and hence clutch plate 120) by the torsion spring 90. The ratchet ramp angle is therefore increased in the anti-clockwise direction to ensure this is the case whilst ensuring the dial-up torque is as low as possible.

The user may now choose to increase the selected dose by continuing to rotate the dose selector 80 in the clockwise direction. The process of overhauling the ratchet interface between the number sleeve 60 and drive sleeve 40 is repeated for each dose increment. Additional energy is stored within the torsion spring 90 for each dose increment and audible and tactile feedback is provided for each increment dialed by the re-engagement of the ratchet teeth. The torque required to rotate the dose selector 80 increases as the torque required to wind up the torsion spring 90 increases. The torque required to overhaul the ratchet in the anti-clockwise direction must therefore be greater than the torque applied to the number sleeve 60 by the torsion spring 90 when the maximum dose has been reached.

If the user continues to increase the selected dose until the maximum dose limit is reached, the number sleeve 60 engages with its maximum dose abutment on the maximum dose abutment of gauge element 110. This prevents further rotation of the number sleeve 60, clutch plate 120 and dose selector 80.

Depending on how many increments have already been delivered by the mechanism, during selection of a dose, the last dose nut 50 may contact its last dose abutment with stop face of the drive sleeve 40. The abutment prevents further relative rotation between the number sleeve 60 and the drive sleeve 40, and therefore limits the dose that can be selected. The position of the last dose nut 50 is determined by the total number of relative rotations between the number sleeve 60 and drive sleeve 40, which have occurred each time the user sets a dose.

With the mechanism in a state in which a dose has been selected, the user is able to deselect any number of increments from this dose. Deselecting a dose is achieved by the user rotating the dose selector 80 anti-clockwise. The torque applied to the dose selector 80 by the user is sufficient, when combined with the torque applied by the torsion spring 90, to overhaul the ratchet interface between the clutch plate 120 and drive sleeve 40 in the anti-clockwise direction. When the ratchet is overhauled, anti-clockwise rotation occurs in the number sleeve 60 (via the clutch plate 120), which returns the number sleeve 60 towards the zero dose position, and unwinds the torsion spring 90. The relative rotation between the number sleeve 60 and drive sleeve 40 causes the last dose nut 50 to return along its helical path, away from the last dose abutment.

With the mechanism in a state in which a dose has been selected, the user is able to activate the mechanism to commence delivery of a dose. Delivery of a dose is initiated by the user depressing the button 70 axially in the distal direction.

When the button 70 is depressed, splines between the button 70 and number sleeve 60 are disengaged, rotationally disconnecting the button 70 and dose selector 80 from the delivery mechanism, i.e. from number sleeve 60, gauge element 110 and torsion spring 90. Splines on the button 70 engage with splines on the housing 10, preventing rotation of the button 70 (and hence the dose selector 80) during dispense. As the button 70 is stationary during dispense, it can be used in the dispense clicker mechanism. A stop feature in the housing 10 limits axial travel of the button 70 and reacts any axial abuse loads applied by the user, reducing the risk of damaging internal components.

The clutch plate 120 and drive sleeve 40 travel axially with the button 70. This engages the splined tooth interface between the drive sleeve 40 and number sleeve 60, preventing relative rotation between the drive sleeve 40 and number sleeve 60 during dispense. The splined tooth interface between the drive sleeve 40 and the housing 10 disengages, so the drive sleeve 40 can now rotate and is driven by the torsion spring 90 via the number sleeve 60, and clutch plate 120.

Rotation of the drive sleeve 40 causes the piston rod 30 to rotate due to their splined engagement, and the piston rod 30 then advances due to its threaded engagement to the housing 10. The number sleeve 60 rotation also causes the gauge element 110 to traverse axially back to its zero position whereby the zero dose abutment stops the mechanism.

Tactile feedback during dose dispense is provided via the compliant cantilever clicker arm integrated into the clutch plate 120. This arm interfaces radially with ratchet features on the inner surface of the button 70, whereby the ratchet tooth spacing corresponds to the number sleeve 60 rotation required for a single increment dispense. During dispense, as the number sleeve 60 rotates and the button 70 is rotationally coupled to the housing 10, the ratchet features engage with the clicker arm to produce an audible click with each dose increment delivered.

Delivery of a dose continues via the mechanical interactions described above while the user continues to depress the button 70. If the user releases the button 70, the clutch spring 130 returns the drive sleeve 40 to its 'at rest' position (together with the clutch plate 120 and button 70), engaging the splines between the drive sleeve 40 and housing 10, preventing further rotation and stopping dose delivery.

During delivery of a dose, the drive sleeve 40 and number sleeve 60 rotate together, so that no relative motion in the last dose nut 50 occurs. The last dose nut 50 therefore travels axially relative to the drive sleeve 40 during dialing only.

Once the delivery of a dose is stopped, by the number sleeve 60 returning to the zero dose abutment, the user may release the button 70, which will re-engage the spline teeth between the drive sleeve 40 and housing 10. The mechanism is now returned to the 'at rest' condition.

At the end of dose dispensing, additional audible feedback is provided in the form of a 'click', distinct from the 'clicks' provided during dispense, to inform the user that the device has returned to its zero position via the interaction of the clicker arm on the number sleeve 60 with the ramp on the drive sleeve 40 and the cam and the recess on the gauge element 110. This embodiment allows feedback to only be created at the end of dose delivery and not created if the device is dialed back to, or away from, the zero position. This end of dose dispensing signal may be in addition or as an alternative to the above mentioned click signal generated by the bosses 111 of the gauge element 110 falling off the axial portion of splines 12 in the housing at the end of dose dispensing.

Figure 7:
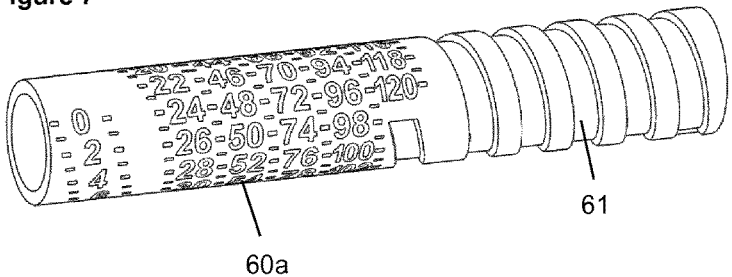
FIG. 7 shows a number sleeve according to a second embodiment of the present disclosure.
Figure 8:
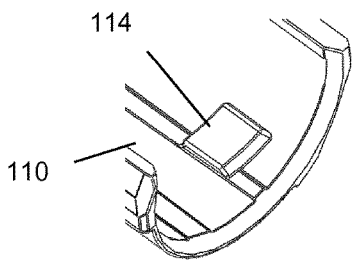
FIG. 8 shows a detail of a gauge element according to the second embodiment of the present disclosure.

In a further exemplary embodiment shown in FIGS. 7 and 8, the gauge element 110 does not deviate from a linear path, but the axial distance by which it moves for each unit increases towards the end of dispense. This is achieved by varying the pitch on the thread of the number sleeve lower 60a. In the embodiment shown in FIG. 7, this pitch is 12 mm at 0 U position (zero position) and decreases gradually to the standard pitch of 6 mm by 24 U. It then remains at 6 mm thereafter. The pitches chosen and the length over which they exist could easily be varied to suit the specification of the device.

For users that require low doses, the increased travel of gauge element 110 at these dose values will make it easier for them to distinguish, and therefore use, the motion of gauge element 110. The pitch of the printed numbers must be adjusted to maintain alignment with the gauge window. The number sleeve 60 with variable pitch thread is shown in FIG. 7. The feature of gauge element 110 which engages with this thread must be made smaller or otherwise adjusted to allow it to interact with a thread of a varying pitch, as shown in FIG. 8.

FIGS. 7 and 8 further show the threaded engagement between number sleeve 60 and gauge element 110 which comprises an outer thread groove 61 of the number sleeve lower 60a and an inner rib portion 114 of gauge element 110. The thread forms are designed such that the two opposite ends of groove 61 form rotational hard stops limiting the relative movement of rib 114 (counter-stops), thus defining a minimum dose position and a maximum dose position of the device.

| Reference Numerals: | |
|---|---|
| 10 | housing (casing) |
| 11a-c | window |
| 12 | track |
| 12a | first section |
| 12b | second section |
| 20 | cartridge holder |
| 30 | piston rod (lead screw) |
| 40 | drive sleeve |
| 50 | nut |
| 60 | dose setting element |
| 60a | number sleeve lower |
| 60b | number sleeve upper |
| 61 | thread (groove) |
| 70 | button |
| 80 | dose selector |
| 90 | torsion spring |
| 100 | cartridge |
| 110 | gauge element |
| 111 | boss |
| 112 | marked region |
| 113 | aperture |
| 114 | thread (rib) |
| 120 | clutch plate |

| Reference Numerals: | |
|---|---|
| 130 | clutch spring |
| 140 | bearing |

The invention claimed is:

1. Non-numerical display for a drug delivery device comprising:
    a housing with at least one window;
    a dosing element movable relative to the housing during one or both of dose setting and dose dispensing; and
    a movable indicator element visible through the at least one window, wherein the indicator element is coupled to one or both of the dosing element and the housing such that a movement of the dosing element relative to the housing is translated into a movement of the indicator element that is not proportional to the movement of the dosing element;
    wherein a continuous movement of the dosing element relative to the housing is translated into an intermittent movement of the indicator element, and
    wherein a continuous movement of the dosing element relative to the housing is translated into an axial movement during a first phase of the movement of the indicator element and into a combined axial and rotational movement during a second phase of the movement of the indicator element.

2. The display according to claim 1, wherein the indicator element is guided within the housing in a track having a first, axially extending portion and a second, helical portion.

3. The display according to claim 2, wherein a transition between the first, axially extending portion of the track and the second, helical portion of the track is stepped.

4. The display according to claim 1, wherein a continuous movement of the dosing element relative to the housing is translated into a movement with a first speed ratio during a first phase of the movement of the indicator element and into a movement with a second speed ratio during a second phase of the movement of the indicator element, wherein the second speed ratio is different from the first speed ratio.

5. The display according to claim 1, wherein the dosing element performs a rotational movement relative to the housing during one or both of dose setting and dose dispensing, and wherein the indicator element is in threaded engagement with the dosing element.

6. The display according to claim 5, wherein a pitch of a thread between the dosing element and the indicator element varies.

7. The display according to claim 1, further comprising a surface provided with a marking, the surface located radially inwards relative to the indicator element, such that the indicator element shields the surface depending on a position of the indicator element relative to the housing.

8. The display according to claim 1, wherein the indicator element comprises at least one region provided with a marking located adjacent to a region of the indicator element without the marking or with a different marking, and wherein an additional window is provided in the housing such that the region provided with the marking is visible through the additional window depending on a position of the indicator element relative to the housing.

9. A drug delivery device for selecting and dispensing a number of user variable doses of a medicament, the device comprising a non-numerical display comprising:

a housing with at least one window;

a dosing element movable relative to the housing during one or both of dose setting and dose dispensing; and a movable indicator element visible through the at least one window, wherein the indicator element is coupled to one or both of the dosing element and the housing such that a movement of the dosing element relative to the housing is translated into a movement of the indicator element that is not proportional to the movement of the dosing element, wherein the dosing element is rotatable relative to the housing between a minimum dose position that is defined by engagement of a rotational stop on the indicator element with a counter-stop on the dosing element, and a maximum dose position that is defined by engagement of a rotational stop on the indicator element with a counter-stop on the dosing element.

10. The drug delivery device according to claim 9, further comprising a numerical display for indicating a dose set by the dosing element.

11. The drug delivery device according to claim 10, wherein the numerical display comprises a series of numbers provided on an outer surface of the dosing element and an aperture or window provided in the indicator element, wherein the series of numbers is visible through the aperture or window of the indicator element and a window of the housing.

12. The drug delivery device according to claim 9, comprising at least one numerical display and at least two non-numerical displays.

\* \* \* \* \*

UNITED STATES PATENT AND TRADEMARK OFFICE
CERTIFICATE OF CORRECTION

PATENT NO. : 10,576,214 B2
APPLICATION NO. : 15/528610
DATED : March 3, 2020
INVENTOR(S) : Robert Frederick Veasey et al.

It is certified that error appears in the above-identified patent and that said Letters Patent is hereby corrected as shown below:

On the Title Page

Item (72), Column 1 (Inventors), Line 11 (approx.), delete "Mickelton" and insert -- Mickleton --

Item (57), Column 2 (Abstract), Line 8, delete "window" and insert -- window. --

Signed and Sealed this
Twenty-fourth Day of November, 2020

Andrei Iancu
*Director of the United States Patent and Trademark Office*